United States Patent
Stefan

(10) Patent No.: US 12,310,613 B2
(45) Date of Patent: May 27, 2025

(54) MEDICAL INSTRUMENT

(71) Applicant: KARL STORZ SE & Co. KG, Tuttlingen (DE)

(72) Inventor: Jochen Stefan, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 413 days.

(21) Appl. No.: 17/966,779

(22) Filed: Oct. 15, 2022

(65) Prior Publication Data

US 2023/0123949 A1    Apr. 20, 2023

(51) Int. Cl.
*A61B 17/29* (2006.01)
*A61B 17/00* (2006.01)

(52) U.S. Cl.
CPC ........ *A61B 17/29* (2013.01); *A61B 17/00234* (2013.01); *A61B 2017/2901* (2013.01); *A61B 2017/2939* (2013.01)

(58) Field of Classification Search
CPC ................. A61B 17/29; A61B 2017/29; A61B 17/00234
See application file for complete search history.

(56) References Cited

U.S. PATENT DOCUMENTS

| | | | | |
|---|---|---|---|---|
| 2003/0236549 | A1* | 12/2003 | Bonadio | A61B 17/29 606/205 |
| 2010/0198253 | A1* | 8/2010 | Jinno | A61B 34/71 606/205 |
| 2010/0331857 | A1* | 12/2010 | Doyle | A61B 34/30 901/29 |

(Continued)

FOREIGN PATENT DOCUMENTS

| | | |
|---|---|---|
| DE | 20 2007 000 425 | 4/2007 |
| DE | 10 2012 105 082 | 12/2013 |

(Continued)

OTHER PUBLICATIONS

May 17, 2022—(DE) Examination Report—App. No. 10 2021 126 895.8.

*Primary Examiner* — Katherine H Schwiker
*Assistant Examiner* — Zehra Jaffri
(74) *Attorney, Agent, or Firm* — Banner & Witcoff, Ltd.

(57) ABSTRACT

The invention relates to a medical instrument having a hollow shaft, whose proximal end can be connected to an operating unit and having a tool tip arranged at the distal end of the shaft having a tool arranged at the distal end of the tool tip, wherein the tool has two jaw parts, which can be pivoted relative to one another and wherein the jaw parts are pivoted via actuating elements which are mounted so as to be axially displaceable in the shaft and which can be actuated on the proximal side via the operating unit and wherein the tool tip can be pivoted via a joint mechanism relative to the longitudinal axis of the shaft.

Figure 1:
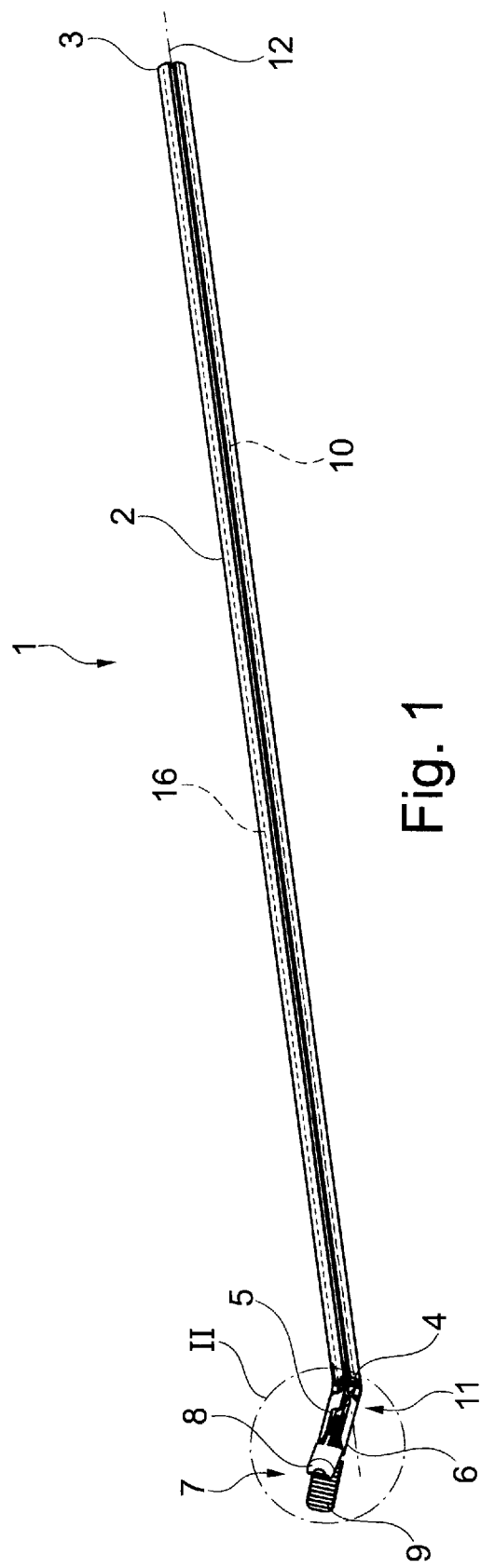

In order to provide a medical instrument, which ensures a uniform transmission of tensile and compressive forces even via the pivot region to the tool tip, it is proposed according to the invention that the pivotable jaw parts are each coupled via an articulated drive element to the distal end of an actuating element mounted so as to be axially displaceable in the shaft such that the articulated drive element spans the region of the joint mechanism between the distal end of the shaft and the proximal end of the tool tip.

6 Claims, 8 Drawing Sheets

(56) References Cited

U.S. PATENT DOCUMENTS

2011/0071561 A1\* 3/2011 Prestel .................. A61B 17/29
606/174

FOREIGN PATENT DOCUMENTS

| DE | 10 2012 212 094 | 1/2014 |
| DE | 10 2016 208 218 | 11/2017 |
| WO | 9743942 | 11/1997 |

\* cited by examiner

MEDICAL INSTRUMENT

This application claims the benefit of and priority to DE 10 2021 126 895.8, entitled "Medical Instrument" filed Oct. 16, 2021, which is hereby incorporated by reference in its entirety for any and all non-limiting purposes.

The invention relates to a medical instrument having a hollow shaft, whose proximal end can be connected to an operating unit and having a tool tip arranged at the distal end of the shaft having a tool arranged at the distal end of the tool tip, wherein the tool has two jaw parts, which can be pivoted relative to one another, and wherein the jaw parts are pivoted via actuating elements, which are mounted so as to be axially displaceable in the shaft and which can be actuated on the proximal side via the operating unit, and wherein the tool tip can be pivoted via a joint mechanism relative to the longitudinal axis of the shaft.

Medical instruments for endoscopic surgery generally have a hollow shaft, at whose proximal end is arranged a handle or operating unit and at whose distal end is arranged a tool consisting of two jaw parts movable relative to one another. In the case of robotic surgery, the operating unit can also be located outside of the OP. In order to be able to cover an effective region that is as large as possible using the tool under the often restrictive working conditions, many endoscopic instruments are designed such that, in addition to the mere actuation of the tool, a tool tip bearing the tool is designed to be bendable with respect to the longitudinal axis of the shaft. In practice, medical instruments of this type are used as hand-operated instruments and also as instruments for a medical telemanipulated robot.

A generic medical instrument is also known from WO 97/43942 A1. In order to be able to actuate the jaw parts at all times even with an angled tool tip, the force is transmitted to the jaw parts via cable strands in this known medical instrument. The use of the cable strands has the advantage that the pivot region between the rigid proximal shaft and the pivotable distal tool tip can be spanned well using cable strands, but the tensile strength of the cable strands is limited and due to the tensile and bending forces occurring in the pivot region, their lifespan is limited. Moreover, virtually no compressive forces can be transmitted via cable strands and the cleaning of cable strands is also very difficult in practice.

Based on this, the object underlying the invention is to provide a medical instrument of the type mentioned at the outset, which ensures a uniform transmission of tensile and compressive forces towards the jaw parts even via the pivot region to the tool tip.

The solution to this object is characterized according to the invention in that the pivotable jaw parts are each coupled via an articulated drive element to the distal end of an actuating element mounted so as to be axially displaceable in the shaft such that the articulated drive element spans the region of the joint mechanism between the distal end of the shaft and the proximal end of the tool tip.

Through the design of the drive for the jaw parts to be pivoted as an articulated drive element, it is, on the one hand, easily possible to follow the angling of the tool tip and, on the other hand however, to also transmit tensile and compressive forces via the pivot region to the tool tip.

For the design of the articulated drive element, it is proposed according to a practical embodiment of the invention that the at least one articulated drive element is designed as a roller chain consisting of a plurality of chain links. The use of a roller chain for transmitting forces has the advantage that a roller chain is a low-maintenance and long-life component, which enables the transmission even of high tensile and compressive forces in the case of sufficient articulation in the pivot region to the tool tip.

In order to pivot the jaw parts, each roller chain is according to the invention mounted in the region of the tool tip on the distal side so as to be articulated at a link chain, which is designed as a bolt chain and which is, for its part, mounted with its free end on one of the jaw parts of the tool, it is also proposed that the planes, about which the chain links of the roller chains and the chain links of the bolt chains can be pivoted relative to one another in an articulated manner, are designed to be offset by 90° in relation to one another.

The roller chains and the bolt chains are connected according to the invention via in each case one coupling element.

In order to be able to achieve the desired 90° offset of the planes, about which the chain links of the roller chains and the chain links of bolt chains can be pivoted relative to one another in an articulated manner, the coupling element has a cardanic structure and a roller chain and a bolt chain can be mounted on the same coupling element so as to be articulated at pivot axes arranged offset by 90° in relation to one another.

Lastly, it is proposed with the invention that a pivot plane stretched by pivoting the tool tip relative to the longitudinal axis of the shaft and a pivot plane stretched by pivoting the jaw parts relative to one another are arranged offset by 90° in relation to one another in order to give the medical instrument according to the invention as many degrees of freedom as possible.

Figure 2:
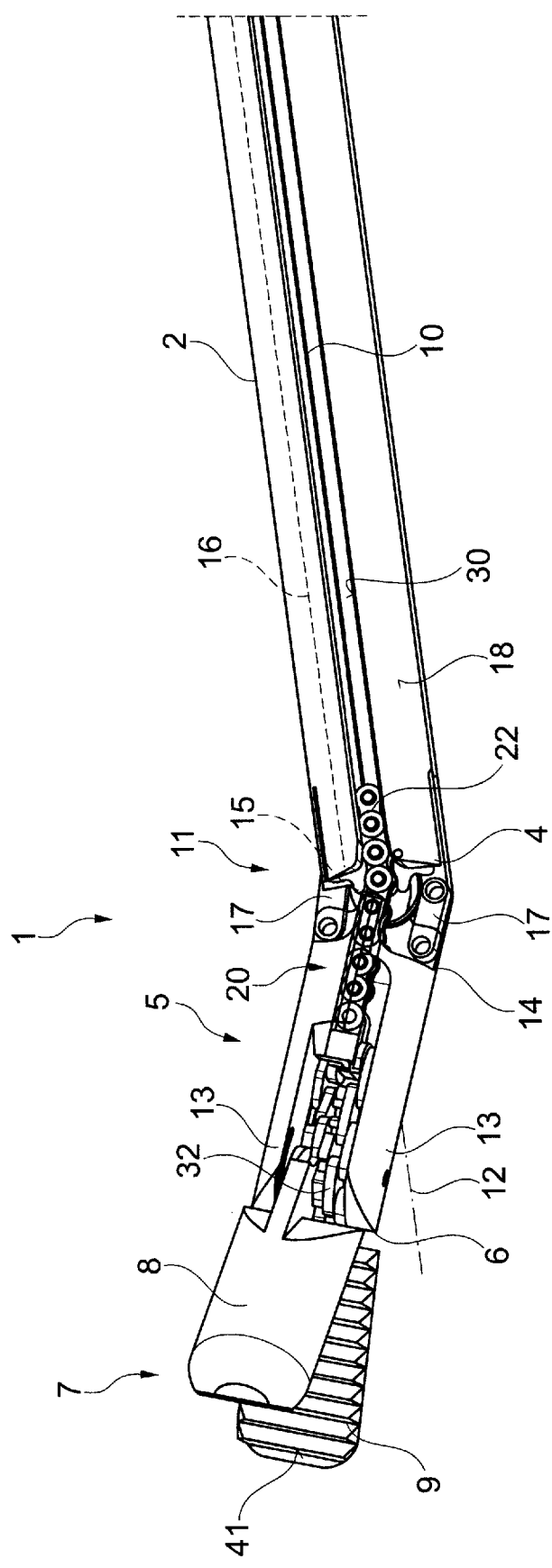
Figure 3:
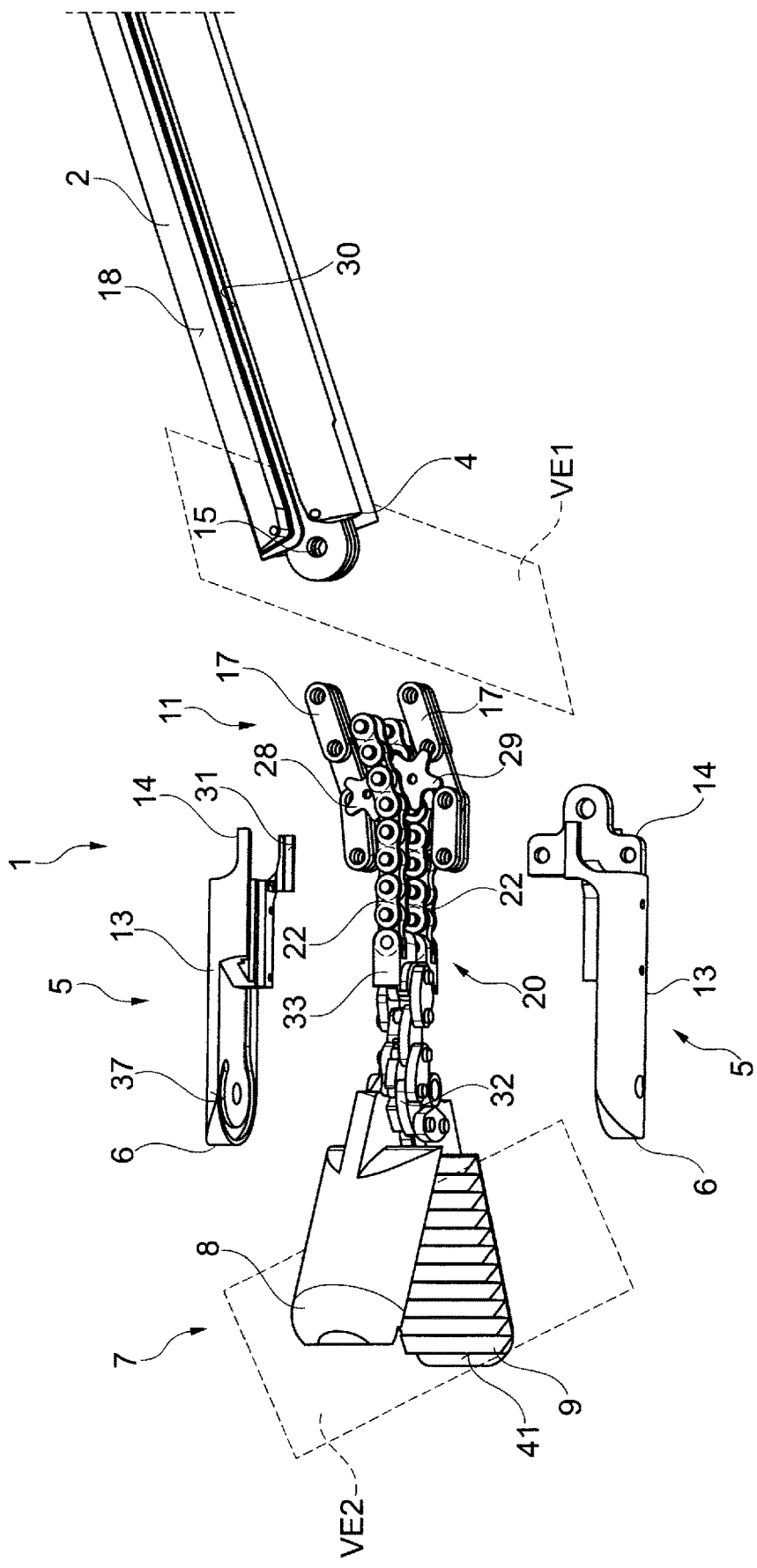
Figure 4:
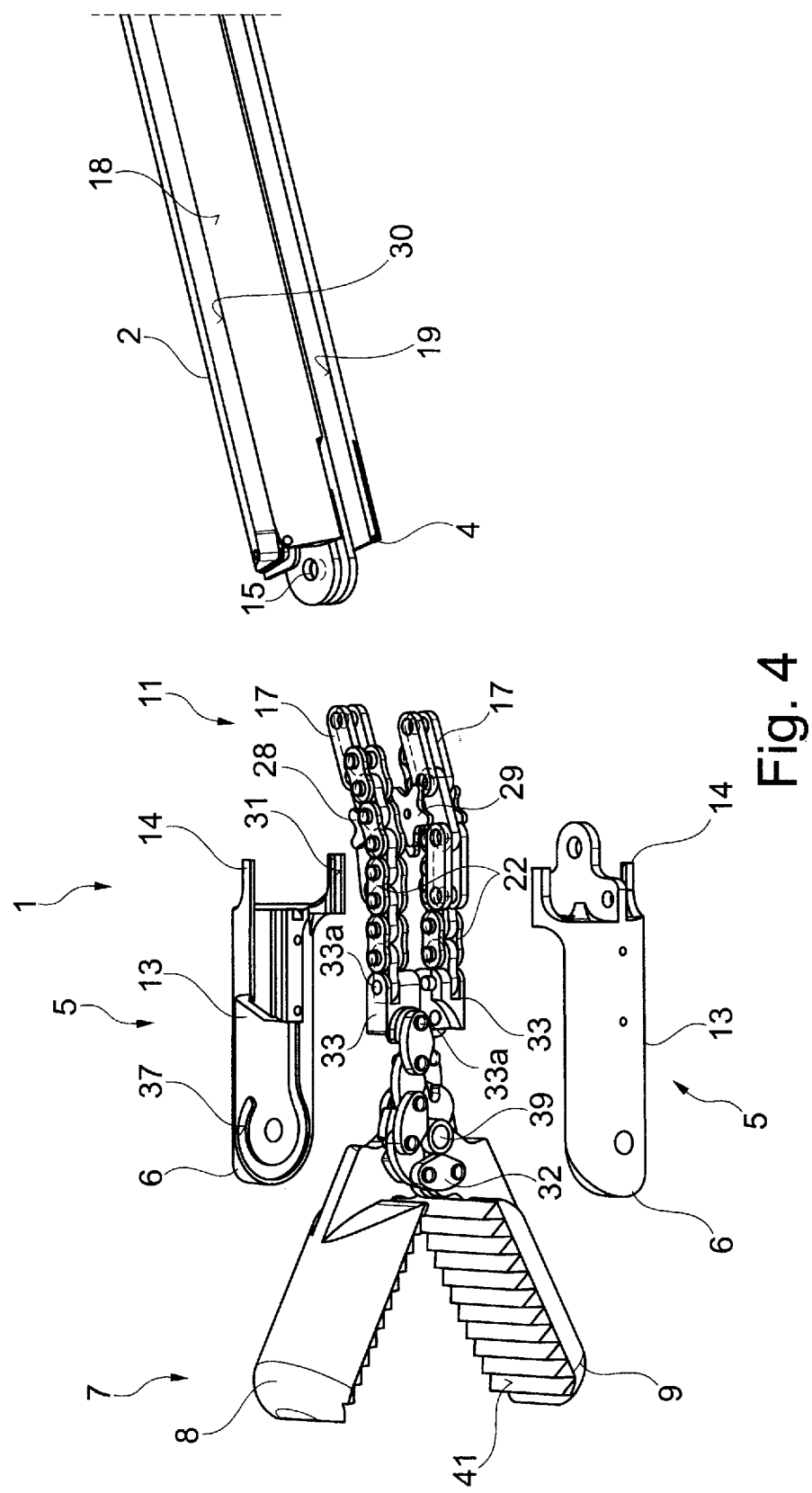
Figure 5:
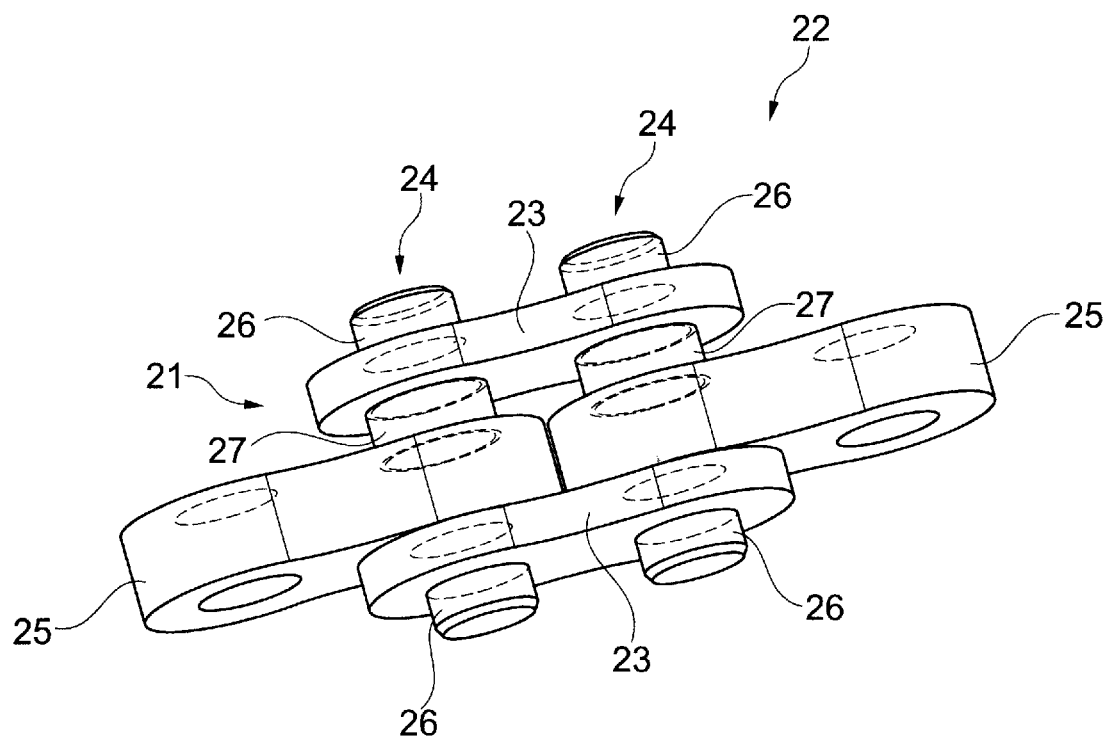
Figure 6:
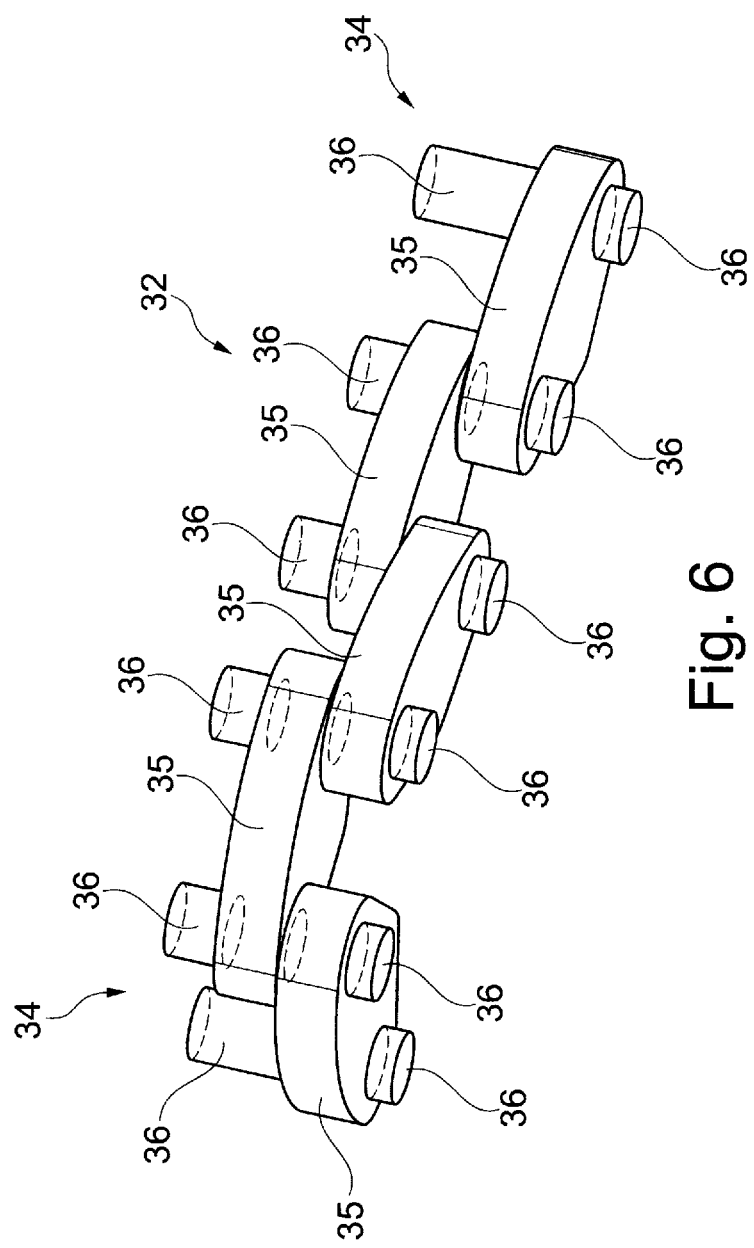
Figure 7:
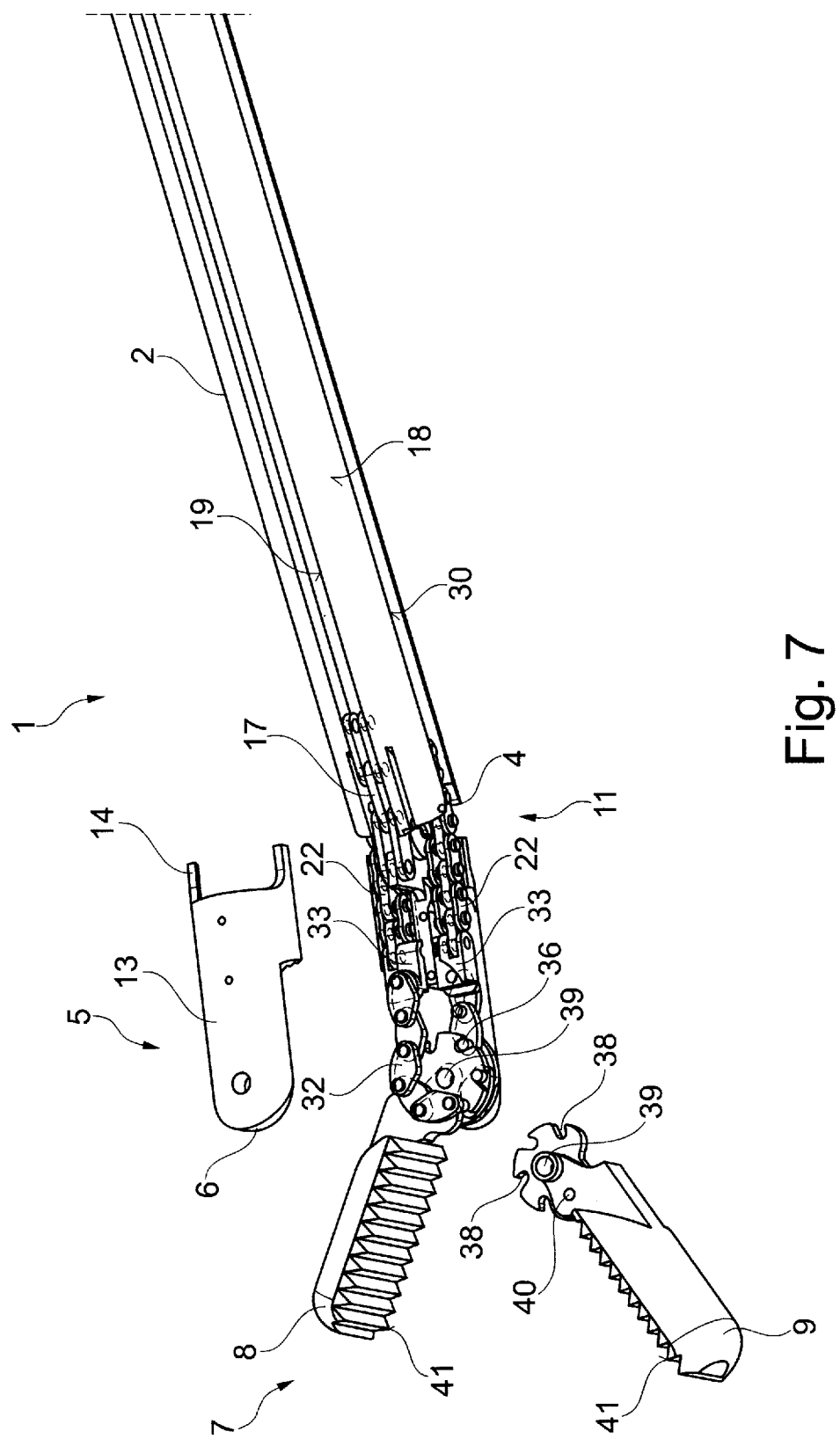
Figure 8:
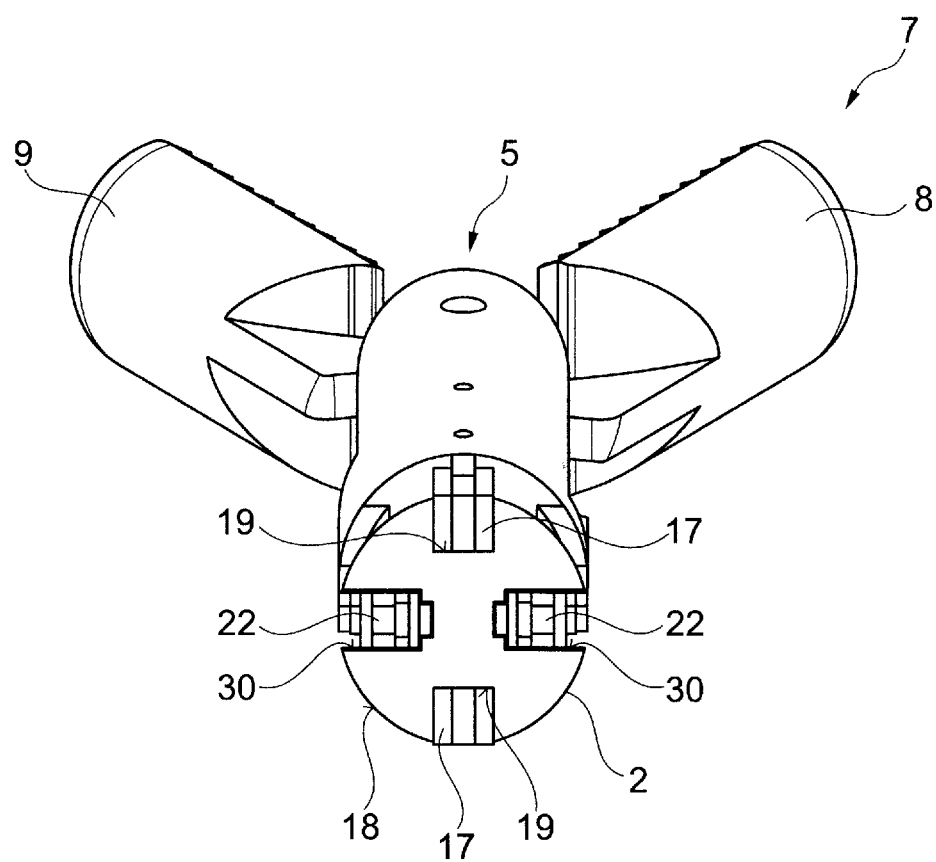

Further features and advantages of the invention will emerge on the basis of the associated drawings, in which an exemplary embodiment of a medical instrument according to the invention is illustrated only by way of example without the invention being limited to this exemplary embodiment. The drawings show:

FIG. 1 a perspective view of a medical instrument according to the invention;

FIG. 2 an enlarged view of the detail II according to FIG. 1;

FIG. 3 a view of the image according to FIG. 2 designed partially as an exploded drawing;

FIG. 4 an enlarged and rotated view of the image according to FIG. 3;

FIG. 5 a perspective top view of a chain link of a roller chain according to the invention;

FIG. 6 a perspective view of a bolt chain according to the invention;

FIG. 7 a further view of the image according to FIG. 2 designed partially as an exploded drawing, and FIG. 8 a cross-section through the distal end of the shaft.

The image of FIG. 1 shows a medical instrument 1 with a hollow shaft 2, whose proximal end 3 can be connected to an operating unit not illustrated and with a tool tip 5 arranged at the distal end 4 of the shaft 2. The operating unit can be a manually-actuated handle or even the control unit of a medical telemanipulated robot.

At the distal end 6 of the tool tip 5 is arranged a tool 7, which has two jaw parts 8 and 9 pivotable relative to one another in the illustrated embodiment, wherein the jaw parts 8 and 9 are pivoted via at least one actuating element 10, which is mounted so as to be axially displaceable in the shaft 2 and which can be actuated on the proximal side via the operating unit. In order to be able to drive the jaw parts 8 and 9 independently of one another, a separate actuating element 10 is in each case preferably provided for each jaw part 8 and 9.

Alternatively to the illustrated embodiment of the tool 7 with two jaw parts 8 and 9 pivotable relative to one another, it is of course also possible to configure the tool 7 such that one jaw part is designed to be rigid and only one jaw part is designed to be pivotable relative to the rigid jaw part.

To increase the degrees of freedom to operate the tool 7, the tool tip 5 bearing the tool 7 can be pivoted upwards and downwards by up to 90° relative to the longitudinal axis 12 of the shaft 2 via a joint mechanism 11.

The pivoting of the tool tip 5 relative to the longitudinal axis 12 of the shaft 2 and the pivoting of the jaw parts 8 and 9 relative to one another is configured such that a pivot plane VE1 stretched by the pivoting of the tool tip 5 relative to the longitudinal axis 12 of the shaft 2 and a pivot plane VE2 stretched by the pivoting of the jaw parts 8 and 9 relative to one another are arranged offset by 90° in relation to one another.

This spatial offset of the two pivot planes VE1 and VE2 in relation to one another also enables an operating range with many degrees of freedom without rotating the medical instrument 1 about the longitudinal axis 12 of the shaft 2.

The tool tip 5 bearing the tool 7 is, as is in particular discernible from FIG. 2, designed to be a fork shape and consists of two partial elements 13, which rest on one another at the proximal end 14 of the tool tip 5 and are spaced apart from one another at the distal end 6 of the tool tip 5 in order not to obstruct the mutual pivoting of the jaw parts 8 and 9 in relation to one another.

The tool tip 5 can be pivoted via the joint mechanism 11 by up to 90° upwards and downwards relative to the longitudinal axis 12 of the shaft 2 about the pivot point 15 (FIG. 3). The tool tip 5 is pivoted via two actuating elements 16, which are mounted so as to be axially displaceable in the shaft 2 and which can be actuated on the proximal side via the operating unit. By means of the tool tip 5, the distal ends of the two actuating elements 16 are connected via in each case one roller chain 17, which consists of a plurality of chain links and which is in each case mounted, on the one hand, at the distal end of the associated actuating element 16 and, on the other hand, at the proximal end 14 of the tool tip 5.

In order to receive and mount in a guided manner the two roller chains 17 of the joint mechanism 11 to pivot the tool tip 5 in the region of the shaft 2, in the outer surface 18 of the distal end 4 of the shaft 2 are designed grooves 19 open outwards and offset by 180° in relation to one another for receiving in a guided manner the roller chains 17, as can be inferred in particular from the image of FIG. 7. The use of the roller chains 17 as drive elements for pivoting the tool tip 5 is advantageous precisely in the transition region from the distal end 4 of the shaft 2 to the proximal end 14 of the tool tip 5 since the individual chain links of the individual roller chains 17 ensure a uniform movement due to their mutual articulated mounting on one another and they ensure the transmission of both compressive forces and tensile forces.

The tool tip 5 of the illustrated medical instrument 1 is pivoted as follows:

To pivot the tool tip 5, one of the actuating elements 16, which are mounted so as to be axially displaceable in the shaft 2, is pulled proximally via the operating unit. This pulling movement of the actuating element 16 is transmitted to the roller chain 17, which is articulated at the distal end of this actuating element 16 and which is mounted with its other end at the proximal end 14 of the tool tip 5. Due to the excentric mounting of the roller chain 17 at the proximal end 14 of the tool tip 5, the pulling movement of the actuating element 16 and of the associated roller chain 17 proximally causes the tool tip 5 to pivot about the pivot point 15.

At the same time, by pivoting the tool tip, the other roller chain 17 together with the associated actuating element 16 is pulled distally.

Alternatively to the use of roller chains 17 as the drive for pivoting the tool tip 5, it is also possible to use cables for this drive since tensile forces are primarily required to pivot the tool tip 5 relative to the longitudinal axis 12 of the shaft 2 via the axial displacement of the two actuating elements 16.

In order to ensure that the jaw parts 8 and 9 can be pivoted in each angle position of the tool tip 5 in relation to the longitudinal axis 12 of the shaft 2 without play and with uniform force transmission between a closed position and any desired open position, the drive for the jaw parts 8 and 9 is designed in the region spanning the joint mechanism 11 between the distal end 4 of the shaft 2 and the proximal end 14 of the tool tip 5 as an articulated drive element 20. The articulation of the drive element 20 thereby ensures the problem-free transition in the case of any angling of the tool tip without the danger of kinking, as may be the case with cables.

In the case of the embodiment of the medical instrument 1 illustrated in the images, the articulated drive element 20 is designed as a roller chain 22 consisting of a plurality of chain links 21, wherein one roller chain 22 is provided in each case for each jaw part 8 and 9.

As is discernible from FIG. 5, each chain link 21 of the roller chain 22 consists of two outer tabs 23 spaced apart from one another, two pins 24 connecting the outer tabs 23 to one another and in each case an intermediate tab 25 mounted on each of the two pins 24 and arranged between the two outer tabs 23. Moreover, all pins 24 of a chain link 21 protrude outwards over one of the outer tabs 23 at least on one side in the same direction forming an overhang 26 and all pins 24 of a chain link 21 have on the same side between the intermediate tab 25 and the inner side of an outer tab 23 a thickened portion 27 enlarging the diameter, via which the intermediate tab 25 is spaced apart from the outer tab 23.

In the region of the joint mechanism 11 between the distal end 5 of the shaft 2 and the proximal end 14 of the tool tip 5 are mounted the two roller chains 22 so as to be guided via in each case one chain wheel pair consisting of two chain wheels 28 and 29, wherein the chain wheels 28 and 29 of each chain wheel pair are arranged in relation to one another such that a chain wheel 28 from above and a chain wheel 29 from below engage at the same chain link 21 of the respective roller chain 22. By arranging the two chain wheels 28 and 29 of each chain wheel pair in different planes relative to the roller chain 22, it is possible to guide and support the roller chain 22 in the region of the joint mechanism 11.

The chain wheels 28 and 29 interact with the individual chain links 21 of the roller chains 22 in such manner that a chain wheel 28 of each chain wheel pair engages at the overhang 26 of the pins 24 over the outer side of the outer tabs 23 and the other chain wheel 29 of the same chain wheel pair engages at the thickened portion 27 of the pins 24.

Since the chain wheels 28 and 29 engage at different diameters of the pins 24, the chain wheels 28 and 29 of each chain wheel pair also have different tooth sizes. This has the advantage that the two chain wheels 28 and 29 engaging at the same chain link 21 can engage only at the points spatially separated from one another, namely either at the overhang 26 or at the thickened portion 27, of each chain link 21 and thus mutual obstruction of the chain wheels 28 and 29 is ruled out.

The two roller chains 22 of the drive for pivoting the jaw parts 8 and 9 are mounted so as to be guided in the region of the shaft 2 via grooves 30 open outwards and offset by 180° in relation to one another in the outer surface 18 of the distal end 4 of the shaft 2, as can be inferred in particular from the image of FIG. 7.

The image of FIG. 8 also shows that the grooves 19 for receiving in a guided manner the roller chains 17 to pivot the tool tip 5 and the grooves 30 for receiving in a guided manner the roller chains 22 to pivot the jaw parts 8 and 9 are arranged offset by 90° in relation to one another in the outer surface 18 of the distal end 4 of the shaft 2.

In order to be able to continue to stably guide the chain links 21 of the roller chains 22 even on the distal side after leaving the chain wheels 28 and 29, on the one hand, all pins 24 have an overhang 26 protruding outwards over the outer tabs 23 on both sides and, on the other hand, on the inner side of the tool tip 5 are designed guide tracks 31 for receiving in a guided manner the overhangs 26 of the pins 24 facing the inner side of the tool tip 5 and protruding over the outer tabs 23.

In order to pivot the jaw parts 8 and 9 via the roller chains 22, each roller chain 22 is mounted in the region of the tool tip 5 on the distal side so as to be articulated at a link chain, which is designed as a bolt chain 32 and which is, for its part, mounted with its free end on one of the jaw parts 8 or 9 of the tool 7.

Since the roller chains 22 serving as a drive for pivoting the jaw parts 8 and 9 are arranged in the transition region between the distal end 4 of the shaft 2 and the proximal end 14 of the tool tip 5 in order to be able to follow the pivoting of the tool tip 5 relative to the longitudinal axis 12 of the shaft 2, the plane, about which the chain links 21 of the roller chains 22 can be pivoted relative to one another in an articulated manner, is also located in the pivot plane VE1 of the tool tip 5.

In order to be able to achieve the desired 90° offset of the pivot plane VE1 of the tool tip 5 and of the pivot plane VE2 of the jaw parts 8 and 9 in relation to one another, as is discernible from FIG. 3, the planes, about which the chain links 21 of the roller chains 22 and the chain links of the bolt chains 32 can be pivoted relative to one another in an articulated manner, are designed to be offset by 90° in relation to one another.

The roller chains 22 and the bolt chains 32 are connected via a coupling element 33 in each case. On the coupling element 33 having a cardanic structure, a roller chain 22 and a bolt chain 32 can be mounted in an articulated manner on pivot axes 33a arranged offset by 90° in relation to one another such that the axial movement of the roller chain 22 is transmitted without play to the bolt chain 32 mounted on the same coupling element 33 offset by 90°.

The bolt chains 32, as discernible from FIG. 6, are structured such that each bolt chain 32 consists of tabs 35 connected to one another in an articulated manner via bolts 34, wherein all bolts 34 forming an overhang 36, protrude outwards over the tabs 35 at least on the side facing the inner side of the tool tip 5.

To receive in a guided manner the overhangs 36 of the bolt chains 32 protruding outwards over the tabs 35 on the side facing the inner side of the tool tip 5, on the inner side of the tool tip 5 are designed guide tracks 37 such that the bolt chains 32 ensure a secure and tilt-free force transmission from the roller chains 22 to the jaw parts 8 and 9.

In the case of the embodiment of the bolt chain 32 illustrated in FIG. 6, all bolts 34 have an overhang 36 protruding outwards over the tabs 35 on both sides.

On the proximal side, receiving portions 38 are designed on the jaw parts 8 and 9 for the overhangs 36 of the bolts 34 opposite the inner side of the tool tip 5. The interaction of the receiving portions 38 on the jaw parts 8 and 9 together with the overhangs 36 of the bolts 34 engaging into the receiving portions 38 is in particular discernible from the image of FIG. 7.

It can also be inferred from the image of FIG. 7 that the proximal end of each jaw part 8 and 9 is designed in a pitch circle shape, wherein the jaw parts 8 and 9 can be pivoted with respect to one another about a common central pivot point 39 and the bolt chains 32 are fastened at the proximal ends of the respective jaw parts 8 and 9 on articulation points 40 arranged excentrically to the pivot point 39. The receiving portions 38 for the overhangs 36 of the bolts 34 are designed to be open radially outwardly in order to facilitate the entry of the overhangs 36 of the bolts 34 into the receiving portion 38.

In order to ensure a positive-locking engagement of the overhangs 36 of the bolts 34 into the receiving portions 38 of the jaw parts 8 and 9 and thus to achieve the best possible transmission of forces to the jaw parts 8 and 9, the receiving portions 38 in the jaw parts 8 and 9 are designed to be bent in a sickle shape in the direction towards a gripping surface 41 of the respective jaw part 8 or 9. The overhangs 36 and the receiving portions 38 act on one another in the manner of mutually engaging tooth wheels, whereby a good transmission of forces from the bolt chains 32 to the jaw parts 8 and 9 is ensured.

The configuration of the receiving portions 38 bent in a sickle shape at the pitch circle-shaped proximal end of the jaw parts 8 and 9 makes it possible for at least two overhangs 36 of the bolt chain 32 to always simultaneously engage in a positive-locking manner into the receiving portions 38 of the jaw parts 8 and 9 and thus there is a uniform and play-free introduction of the tensile or compressive force of the bolt chains 32 to the jaw parts 8 and 9.

The guide tracks 37 for receiving the overhangs 36 of the bolt chains 32 protruding outwards over the tabs 35 on the side facing the inner side of the tool tip 5 are designed to be bent in a sickle shape on the distal side, as can be inferred in particular from the image of FIG. 4, in order to be able to guide the bolt chains 32 over the entire pivot region of the jaw parts 8 and 9 without tilting.

Together with the fork-shaped structure of the distal end 6 of the tool tip 5, the previously described structure of the drive for pivoting the jaw parts 8 and 9 via the bolt chains 32 makes it possible to pivot the individual jaw parts 8 and 9 by up to 270° in the case of a tool tip 5 angled with respect to the longitudinal axis 12 of the shaft 2.

Alternatively to the design of the receiving portions 38 bent in a sickle shape, it is also possible to design the receiving portions 38 in a triangular shape.

The jaw parts 8 and 9 of the illustrated medical instrument 1 are pivoted as follows:

To pivot the jaw parts 8 or 9, one of the actuating elements 10, which are mounted so as to be axially displaceable in the shaft 2, is pulled proximally or pressed distally via the operating unit. This pulling movement of the actuating element 10 is transmitted to the roller chain 22, which is articulated at the distal end of this actuating element 10 and which is, for its part, coupled on the distal side to the bolt chain 32 mounted at the proximal end of the jaw part 8 or 9 to be actuated. The movement of the roller chain 22 is guided further distally without play and uniformly in any angle position of the tool tip 5 via the chain wheels 28 and 29 arranged in the pivot region of the tool tip 5. The additional guidance of the roller chain 22 in the guide track 31 at the proximal end 14 of the tool tip and of the bolt chain 32 in the guide track 37 designed at the distal end 6 of the tool tip 5 ensures a tilt-free and uniform transmission of forces towards the respective jaw part 8 or 9 to be actuated along the entire length of the tool tip 5.

At the distal end 6 of the tool tip 5, the overhangs 36 of the bolts 34 of the bolt chain 32 engage into the corresponding receiving portions 38 of the jaw part 8 or 9 to be actuated and cause the actuated jaw part 8 or 9 to pivot relative to the other jaw part 9 or 8.

A medical instrument 1 designed as previously described is characterized in that, regardless of the angle position of the tool tip 5 relative to the longitudinal axis 12 of the shaft, a uniform transmission of tensile and compressive forces is ensured at all times via the pivot region to the tool tip 5.

List of Reference Numerals
- 1 Medical instrument
- 2 Shaft
- 3 Proximal end (shaft)
- 4 Distal end (shaft)
- 5 Tool tip
- 6 Distal end (tool tip)
- 7 Tool
- 8 Jaw part
- 9 Jaw part
- 10 Actuating element
- 11 Joint mechanism
- 12 Longitudinal axis (shaft)
- 13 Partial element (tool tip)
- 14 Proximal end (tool tip)
- 15 Pivot point
- 16 Actuating element
- 17 Roller chain
- 18 Outer surface (shaft)
- 19 Groove
- 20 Articulated drive element
- 21 Chain link
- 22 Roller chain
- 23 Outer tab
- 24 Pin
- 25 Intermediate tab
- 26 Overhang
- 27 Thickened portion
- 28 Chain wheel
- 29 Chain wheel
- 30 Groove
- 31 Guide track
- 32 Bolt chain
- 33 Coupling element
- 33a Pivot axis
- 34 Bolt
- 35 Tab
- 36 Overhang
- 37 Guide track
- 38 Receiving portion
- 39 Pivot point
- 40 Articulation point
- 41 Gripping surface
- VE1 Pivot plane (tool tip)
- VE2 Pivot plane (jaw parts)

The invention claimed is:

1. A medical instrument comprising: a hollow shaft having a proximal end and a distal end, and having a tool tip arranged on the distal end of the shaft having a tool arranged on a distal end of the tool tip, wherein the tool has two jaw parts, which can be pivoted relative to one another and wherein the jaw parts are pivoted via one or more actuating elements, which are mounted so as to be axially displaceable in the shaft and which can be actuated on the proximal end, and wherein the tool tip can be pivoted via a joint mechanism relative to a longitudinal axis of the shaft,
characterized in that the jaw parts are each coupled via an articulated drive element to a distal end of one of the one or more actuating elements such that the articulated drive element spans a region of the joint mechanism between the distal end of the shaft and a proximal end of the tool tip, wherein the articulated drive element is a roller chain that is mounted so as to be guided in a region of the tool tip and articulated as a link chain and wherein the link chain is designed as a bolt chain.

2. The medical instrument according to claim 1, characterized in that the bolt chain is mounted with a free end on one of the jaw parts of the tool.

3. The medical instrument according to claim 2, characterized in that one or more planes about which the chain links of the roller chains and one or more chain links of the bolt chains can be pivoted relative to one another in an articulated manner, are designed to be offset by 90° in relation to one another.

4. The medical instrument according to claim 2, characterized in that the roller chain is mounted via a coupling element on the associated bolt chain.

5. The medical instrument according to claim 4, characterized in that the coupling element has a cardanic structure and the roller chain and the bolt chain can be mounted on the coupling element so as to be articulated at pivot axes arranged offset by 90° in relation to one another.

6. The medical instrument according to claim 1, characterized in that a pivot plane (VE1) stretched by pivoting the tool tip relative to the longitudinal axis of the shaft and a pivot plane (VE2) stretched by pivoting the jaw parts relative to one another are arranged offset by 90° in relation to one another.

* * * * *